United States Patent
Frick et al.

(12) 
(10) Patent No.: US 6,303,639 B1
(45) Date of Patent: Oct. 16, 2001

(54) PROPANOLAMINE DERIVATIVES SUBSTITUTED BY HETEROCYCLIC RADICALS, PROCESSES FOR THEIR PREPARATION, PHARMACEUTICALS COMPRISING THESE COMPOUNDS AND THEIR USE

(75) Inventors: Wendelin Frick, Hünstetten-Beuerbach; Reinhard Kirsch, Braunschweig; Heiner Glombik, Hofheim; Hubert Heuer, Schwabenheim, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/407,973

(22) Filed: Sep. 29, 1999

(30) Foreign Application Priority Data

Oct. 2, 1998 (DE) .................................. 198 45 402

(51) Int. Cl.[7] .................. A61K 31/443; C07D 409/12
(52) U.S. Cl. .................. 514/342; 514/340; 514/338; 514/333; 514/212; 514/256; 514/314; 514/357; 514/332; 546/269.7; 546/271.1; 546/256; 546/255; 546/270.1; 546/176; 544/333
(58) Field of Search .................. 514/342, 314, 514/340, 357, 338, 332, 333, 212, 256; 546/269.7, 271.1, 256, 255, 270.1, 176; 544/333

(56) References Cited

U.S. PATENT DOCUMENTS 5,874,451   2/1999   Glombik et al. .................. 514/357

FOREIGN PATENT DOCUMENTS 0 869 121 A1   10/1998   (EP) .

OTHER PUBLICATIONS

CA 120:173483 "Lipid metabolism–improving compositions containing glutathione derivatives" Ohmori et al., 1994.*
English Abstract, Derwent No. 98–508454.
Huang, Y. and Hall, IH, "Hypolipidemic effects of α, β, and γ–alkylaminophenone analogs in rodents," *Eur. J. Med. Chem.*, vol. 31, 1996, pp. 281–290.
International Search Report, dated Dec. 21, 1999.

* cited by examiner

*Primary Examiner*—Jane Fan
(74) *Attorney, Agent, or Firm*—Finnegan, Henderson, Farabow, Garrett & Dunner, L.L.P.

(57) ABSTRACT

Substituted propanolamine derivatives and pharmaceutically tolerated salts and physiologically functional derivatives thereof are described.

Also described are compounds of formula (I),

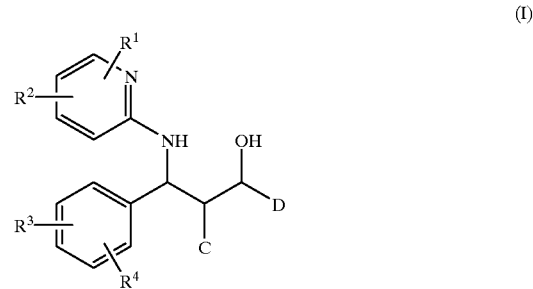

in which the radicals have the meanings given in the specification and claims, and physiologically tolerated salts and physiologically functional derivatives thereof, and processes for their preparation, are described. The compounds are suitable, for example, as hypolipidemic agents.

12 Claims, No Drawings

PROPANOLAMINE DERIVATIVES SUBSTITUTED BY HETEROCYCLIC RADICALS, PROCESSES FOR THEIR PREPARATION, PHARMACEUTICALS COMPRISING THESE COMPOUNDS AND THEIR USE

Under the provisions of Section 119 of 35 U.S.C., Applicants hereby claim the benefit of the filing date of Federal Republic of Germany Patent Application Number 19845402.3, filed Oct. 2, 1998, which Application is hereby incorporated by reference.

The present invention relates to substituted propanolamine derivatives and pharmaceutically tolerated salts and physiologically functional derivatives thereof.

Several classes of active compounds have already been described for treatment of adiposity and disturbances in lipid metabolism:

polymeric adsorbers, such as cholestyramine;
benzothiazepines (WO 93/16055);
bile acid dimers and conjugates (EP 0 489 423); and
4-amino-2-ureido-pyrimidine-5-carboxylic acid amides (EP 0 557 879).

The present invention is based on the object of providing further compounds displaying a therapeutically valuable hypolipidemic action. The present invention therefore relates to compounds of formula (I) or salts thereof:

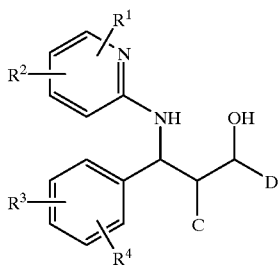

(I)

wherein:

C is phenyl, pyridyl, thienyl, furyl, pyrimidyl, indolyl, thiazolyl, imidazolyl, coumarinyl, phthalimidyl, quinolyl, piperazinyl, tetrazolyl, triazolyl, oxazolyl, isoxazolyl, isothiazolyl, or thieno-, pyridino-, or benzo-fused derivatives thereof, wherein the aromatic or heteroaromatic radical is unsubstituted, or mono- or disubstituted by fluorine, chlorine, bromine, iodine, —OH, —CF$_3$, —NO$_2$, —CN, —(C$_1$–C$_8$)-alkoxy, —(C$_1$–C$_8$)-alkyl, —NH$_2$, —NH—R$^9$, —N(R$^9$)R$^{10}$, —CHO, —COOH, —COOR$^{11}$, —(C═O)—R$^{12}$, —(C$_1$–C$_6$)-alkyl-OH, —(C$_1$–C$_6$)-alkyl(—OH)-phenyl, —(C$_1$–C$_6$)-alkyl-CF$_3$, —(C$_1$–C$_6$)-alkyl-NO$_2$, —(C$_1$–C$_6$)-alkyl-CN, —(C$_1$–C$_6$)-alkyl-NH$_2$, —(C$_1$–C$_6$)-alkyl-NH—R$^9$, —(C$_1$–C$_6$)-alkyl-N(R$^9$)R$^{10}$, —(C$_1$–C$_6$)-alkyl-CHO, —(C$_1$–C$_6$)-alkyl-COOH, —(C$_1$–C$_6$)-alkyl-COOR$^{11}$, —(C$_1$–C$_6$)-alkyl-(C═O)—R$^{12}$, —O—(C$_1$–C$_6$)-alkyl-OH, —O—(C$_1$–C$_6$)-alkyl-CF$_3$, —O—(C$_1$–C$_6$)-alkyl-NO$_2$, —O—(C$_1$–C$_6$)-alkyl-CN, —O—(C$_1$–C$_6$)-alkyl-NH$_2$, —O—(C$_1$–C$_6$)-alkyl-NH—R$^9$, —O—(C$_1$–C$_6$)-alkyl-N(R$^9$)R$^{10}$, —O—(C$_1$–C$_6$)-alkyl-CHO, —O—(C$_1$–C$_6$)-alkyl-COOH, —O—(C$_1$–C$_6$)-alkyl-COOR$^{11}$, —O—(C$_1$–C$_6$)-alkyl-(C═O)—R$^{12}$, —N—SO$_3$H, —SO$_2$—CH$_3$, or —O—(C$_1$–C$_6$)-alkyl-O—(C$_1$–C$_6$)-alkylphenyl, wherein one or more hydrogen(s) in the alkyl radicals is optionally replaced by fluorine;

D is phenyl, pyridyl, thienyl, furyl, pyrimidyl, indolyl, thiazolyl, imidazolyl, coumarinyl, phthalimidyl, quinolyl, piperazinyl, tetrazolyl, triazolyl, oxazolyl, isoxazolyl, isothiazolyl, or 4,5,6,7-tetrahydrobenzisoxazole, or thieno-, pyridino-, or benzo-fused derivatives thereof, wherein the aromatic or heteroaromatic radical is unsubstituted, or is mono- or disubstituted by fluorine, chlorine, bromine, iodine, —OH, —CF$_3$, —NO$_2$, —CN, —(C$_1$–C$_8$)-alkoxy, —(C$_1$–C$_8$)-alkyl, —NH$_2$, —NH—R$^9$, —N(R$^9$)R$^{10}$, —CHO, —COOH, —COOR$^{11}$, —(C═O)—R$^{12}$, —(C$_1$–C$_6$)-alkyl-OH, —(C$_1$–C$_6$)-alkyl(—OH)-phenyl, —(C$_1$–C$_6$)-alkyl-CF$_3$, —(C$_1$–C$_6$)-alkyl-NO$_2$, —(C$_1$–C$_6$)-alkyl-CN, —(C$_1$–C$_6$)-alkyl-NH$_2$, —(C$_1$–C$_6$)-alkyl-NH—R$^9$, —(C$_1$–C$_6$)-alkyl-N(R$^9$)R$^{10}$, —(C$_1$–C$_6$)-alkyl-CHO, —(C$_1$–C$_6$)-alkyl-COOH, —(C$_1$–C$_6$)-alkyl-COOR$^{11}$, —(C$_1$–C$_6$)-alkyl-(C═O)—R$^{12}$, —O—(C$_1$–C$_6$)-alkyl-OH, —O—(C$_1$–C$_6$)-alkyl-CF$_3$, —O—(C$_1$–C$_6$)-alkyl-NO$_2$, —O—(C$_1$–C$_6$)-alkyl-CN, —O—(C$_1$–C$_6$)-alkyl-NH$_2$, —O—(C$_1$–C$_6$)-alkyl-NH—R$^9$, —O—(C$_1$–C$_6$)-alkyl-N(R$^9$)R$^{10}$, —O—(C$_1$–C$_6$)-alkyl-CHO, —O—(C$_1$–C$_6$)-alkyl-COOH, —O—(C$_1$–C$_6$)-alkyl-COOR$^{11}$, —O—(C$_1$–C$_6$)-alkyl-(C═O)—R$^{12}$, —N—SO$_3$H, —SO$_2$—CH$_3$, —(C$_0$–C$_6$)-alkyl-pyridyl, —O—(C$_1$–C$_6$)-alkyl-O—(C$_1$–C$_6$)-alkylphenyl, or —(C$_0$–C$_6$)-alkylphenyl, wherein the phenyl radicals are unsubstituted, or mono- or di-substituted by F, Cl, —CF$_3$, —OCF$_3$, —(C$_1$–C$_6$)-alkyl, or —O—(C$_1$–C$_6$)-alkyl and wherein one or more hydrogen(s) in the alkyl radicals is optionally replaced by fluorine;

with the proviso that C and D do not simultaneously have the following meaning:
C=phenyl and D=phenyl;
C=phenyl and D=pyridyl;
C=pyridyl and D=phenyl;
C=pyridyl and D=pyridyl;

R$^1$, R$^2$, R$^3$, R$^4$ each independently of one another is hydrogen, fluorine, chlorine, bromine, iodine, —OH, —CF$_3$, —NO$_2$, —CN, —(C$_1$–C$_8$)-alkoxy, —(C$_1$–C$_8$)-alkyl, —NH$_2$, —NH—R$^9$, —N(R$^9$)R$^{10}$, —CHO, —COOH, —COOR$^{11}$, —(C═O)—R$^{12}$, —(C$_1$–C$_6$)-alkyl-OH, —(C$_1$–C$_6$)-alkyl(—OH)-phenyl, —(C$_1$–C$_6$)-alkyl-CF$_3$, —(C$_1$–C$_6$)-alkyl-NO$_2$, —(C$_1$–C$_6$)-alkyl-CN, —(C$_1$–C$_6$)-alkyl-NH$_2$, —(C$_1$–C$_6$)-alkyl-NH—R$^9$, —(C$_1$–C$_6$)-alkyl-N(R$^9$)R$^{10}$, —(C$_1$–C$_6$)-alkyl-CHO, —(C$_1$–C$_6$)-alkyl-COOH, —(C$_1$–C$_6$)-alkyl-COOR$^{11}$, —(C$_1$–C$_6$)-alkyl-(C═O)—R$^{12}$, —O—(C$_1$–C$_6$)-alkyl-OH, —O—(C$_1$–C$_6$)-alkyl-CF$_3$, —O—(C$_1$–C$_6$)-alkyl-NO$_2$, —O—(C$_1$–C$_6$)-alkyl-CN, —O—(C$_1$–C$_6$)-alkyl-NH$_2$, —O—(C$_1$–C$_6$)-alkyl-NH—R$^9$, —O—(C$_1$–C$_6$)-alkyl-N(R$^9$)R$^{10}$, —O—(C$_1$–C$_6$)-alkyl-CHO, —O—(C$_1$–C$_6$)-alkyl-COOH, —O—(C$_1$–C$_6$)-alkyl-COOR$^{11}$, —O—(C$_1$–C$_6$)-alkyl-(C═O)—R$^{12}$, —N—SO$_3$H, —SO$_2$—CH$_3$, or —O—(C$_1$–C$_6$)-alkyl-O—(C$_1$–C$_6$)-alkylphenyl, wherein one or more hydrogen(s) in the alkyl radicals is optionally replaced by fluorine;

R$^9$ to R$^{12}$ each independently of one another is hydrogen or —(C$_1$–C$_8$)-alkyl.

Preferred compounds of formula (I) or salts thereof are those in which one or more radical(s) has or have the following meaning:

C is phenyl, pyridyl, thienyl, furyl, pyrimidyl, indolyl, thiazolyl, imidazolyl, coumarinyl, phthalimidyl, quinolyl, piperazinyl, tetrazolyl, triazolyl, oxazolyl, isoxazolyl, isothiazolyl or benzo-fused derivatives thereof, wherein the aromatic or heteroaromatic radical is unsubstituted, or mono- or disubstituted by fluorine, chlorine, bromine, iodine, —OH, —CF$_3$, —NO$_2$, —CN, —(C$_1$–C$_8$)-alkoxy, —(C$_1$–C$_8$)-alkyl, —(C$_3$–C$_6$)-cycloalkyl, —NH$_2$, —CHO, —COOH, or —OCF$_3$;

D is phenyl, pyridyl, thienyl, furyl, pyrimidyl, indolyl, thiazolyl, imidazolyl, coumarinyl, phthalimidyl, quinolyl, piperazinyl, tetrazolyl, triazolyl, oxazolyl, isoxazolyl, isothiazolyl or benzo-fused derivatives thereof, wherein the aromatic or heteroaromatic radical is unsubstituted, or mono- or disubstituted by fluorine, chlorine, bromine, iodine, —OH, —CF$_3$, —NO$_2$, —CN, —(C$_1$–C$_8$)-alkoxy, —(C$_1$–C$_8$)-alkyl, —(C$_3$–C$_6$)-cycloalkyl, —NH$_2$, —CHO, —COOH, or —OCF$_3$;

with the proviso that C and D do not simultaneously have the following meaning:
C=phenyl and D=phenyl;
C=phenyl and D=pyridyl;
C=pyridyl and D=phenyl;
C=pyridyl and D=pyridyl;

$R_1$, $R_2$, $R^3$, $R^4$ each independently of one another is hydrogen, fluorine, chlorine, bromine, iodine, —OH, —CF$_3$, —OCF$_3$, —NO$_2$, —CN, —(C$_1$–C$_8$)-alkoxy, —(C$_1$–C$_8$)-alkyl, —(C$_3$–C$_6$)-cycloalkyl, —NH$_2$, —NH—R$^9$, —N(R$^9$)R$^{10}$, —CHO, —COOH, —COOR$^{11}$, or —(C═O)—R$^{12}$, wherein one or more hydrogen(s) in the alkyl radicals is optionally replaced by fluorine;

$R^9$ to $R^{12}$ each independently of one another is hydrogen or —(C$_1$–C$_8$)-alkyl.

Particularly preferred compounds of formula (I) or salts thereof are those in which one or more radical(s) has or have the following meaning:

C is phenyl, pyridyl, thienyl, pyrimidyl, indolyl, thiazolyl, quinolyl, oxazolyl, or isoxazolyl, wherein the aromatic or heteroaromatic radical is unsubstituted, or is mono- or disubstituted by fluorine, chlorine, bromine, or —(C$_1$–C$_8$)-alkyl;

D is phenyl, pyridyl, thienyl, pyrimidyl, indolyl, thiazolyl, quinolyl, imidazolyl, triazolyl, oxazolyl or isoxazolyl, wherein the aromatic or heteroaromatic radical is unsubstituted, or is mono- or disubstituted by fluorine, chlorine, bromine, or —(C$_1$–C$_8$)-alkyl;

with the proviso that C and D do not simultaneously have the following meaning:
C=phenyl and D=phenyl;
C=phenyl and D=pyridyl;
C=pyridyl and D=phenyl;
C=pyridyl and D=pyridyl;

$R^1$, $R^2$, $R^3$, $R^4$ each independently of one another is hydrogen, fluorine, chlorine, bromine, iodine, —OH, —CF$_3$, —OCF$_3$, —NO$_2$, —CN, —(C$_1$–C$_8$)-alkoxy, —(C$_1$–C$_8$)-alkyl, —(C$_3$–C$_6$)-cycloalkyl, —NH$_2$, —NH—R$^9$, —N(R$^9$)R$^{10}$, —CHO, —COOH, —COOR$^{11}$, or —(C═O)—R$^{12}$, wherein one or more hydrogen(s) in the alkyl radicals is optionally replaced by fluorine;

$R^9$ to $R^{12}$ each independently of one another is hydrogen or —(C$_1$–C$_8$)-alkyl.

The term alkyl is defined as meaning straight-chain or branched hydrocarbon chains. The phrase "each independently of one another is" means each radical is individually selected without reference to the selection of the other radicals. Therefore, this phrase includes situations where the radicals are all identical to one another, where they are all different from one another, and where some radicals are identical to one another and others are different.

The invention furthermore relates to a process for the preparation of compounds of formula (I) which comprises the following reaction scheme:

Process A
Scheme 1

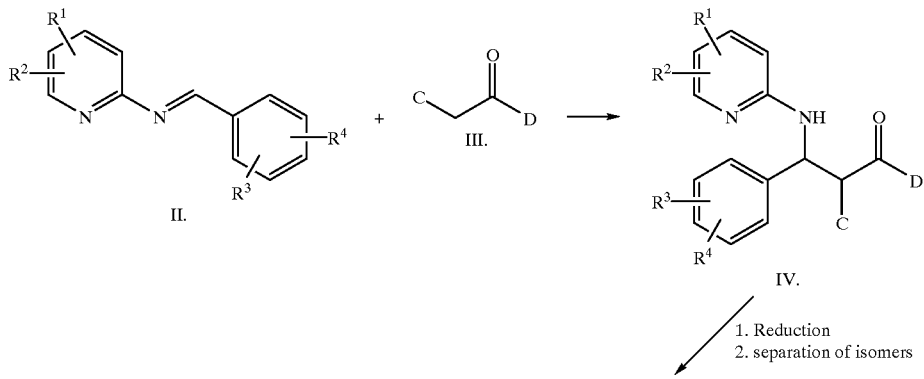

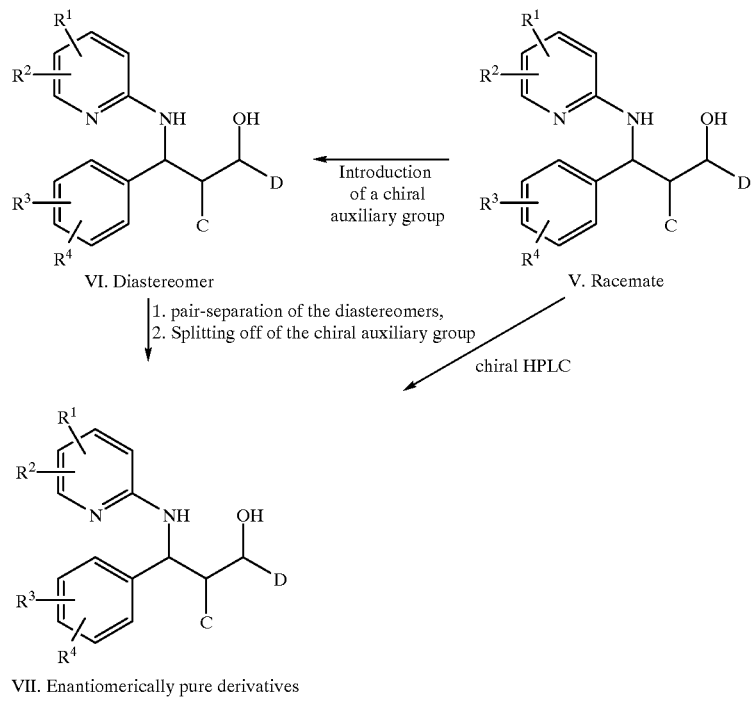

VII. Enantiomerically pure derivatives

Compounds of type IV are obtained by reacting o-, m- or p-substituted imines of type II with the ketone III. The reaction can be carried out, for example, by mixing the two compounds in bulk, without a solvent, and then heating the mixture, or in a suitable solvent, such as ethanol, tetrahydrofuran (THF), toluene, diglyme, or tetradecane, at temperatures from 20° C. to 150° C.

The keto compounds of type IV are reduced to hydroxy compounds of type V with $NaBH_4$ or another suitable reducing agent in a suitable solvent, such as methanol, THF, or THF/water, at temperatures between −30° C. and +40° C. During the reduction, up to four isomer mixtures (racemates) are obtained as reaction products. The various racemates can be separated from one another by fractional crystallization or by silica gel chromatography.

The racemic compounds of type V thus obtained can be further separated into their enantiomers. The splitting of racemates of V into enantiomers of type VII can be carried out by chromatography over chiral column material or by processes known from the literature using optically active auxiliary reagents (J. Org. Chem. 44, (1979) 4891).

Because of their higher solubility in water compared with the starting or base compounds, pharmaceutically tolerated salts are particularly suitable for medical applications. These salts must have a pharmaceutically tolerated anion or cation. Suitable pharmaceutically tolerated acid addition salts of the compounds and salts according to the present invention are salts of inorganic acids, such as hydrochloric, hydrobromic, phosphoric, metaphosphoric, nitric, sulfonic and sulfuric acid, and of organic acids, such as, acetic, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric, and trifluoroacetic acid. For medical purposes, the chlorine salt is generally used. Suitable pharmaceutically tolerated basic salts are ammonium salts, alkali metal salts (such as sodium and potassium salts) and alkaline earth metal salts (such as magnesium and calcium salts).

Salts with an anion which is not pharmaceutically tolerated also belong in the context of the invention as beneficial intermediate products for the preparation or purification of pharmaceutically tolerated salts and/or for use in nontherapeutic, for example, in vitro applications.

The term "physiologically functional derivative" used here designates any physiologically tolerated derivative of a compound of formula (I) according to the invention, for example an ester, which, when administered to a mammal, such as, for example, man, is capable of forming (directly or indirectly) a compound of formula (I) or an active metabolite thereof.

The physiologically functional derivatives also include prodrugs of the compounds according to the invention. Such prodrugs can be metabolized in vivo to give a compound according to the invention. These prodrugs of the compounds of the formula (I) are, for example esters, amides, aldehydes or alcohols obtainable from carboxy groups, or acyl derivatives like $(C_1-C_6)$-alkylcarbonyl, $(C_1-C_6)$-alkyloxycarbonyl, or aryl-$(C_1-C_4)$-alkyloxycarbonyl derivatives obtainable from acylatable groups including amino groups, imino groups, guanidino groups and amidino groups. These prodrugs can be active themselves or inactive.

The compounds according to the invention can also exist in various polymorphous forms, for example as amorphous and crystalline polymorphous forms. All the polymorphous forms of the compounds according to the invention belong in the context of the invention and are a further aspect of the invention.

In the following text, all references to "compound(s) according to formula (I)" relate to compound(s) of formula (I) as described above and their salts, solvates and physiologically functional derivatives as described herein.

The amount of a compound according to formula (I) necessary to achieve the desired biological effect depends on a number of factors, for example the specific compound chosen, the intended use, the mode of administration and the clinical condition of the patient. In general, the daily dose is in the range from 0.3 mg to 100 mg (typically from 3 mg to 50 mg) per day per kilogram of body weight, for example 3–10 mg/kg/day. An intravenous dose can be, for example, in the range from 0.3 mg to 1.0 mg/kg, which can suitably be administered as an infusion of 10 ng to 100 ng per kilogram per minute. Suitable infusion solutions for this purpose can comprise, for example, from 0.1 ng to 10 mg, typically from 1 ng to 10 mg per milliliter. Individual doses can comprise, for example, from 1 mg to 10 g of the active compound. Ampoules for injections can thus contain, for example, from 1 mg to 100 mg, and individual dose formulations which can be administered orally, such as, for example, tablets or capsules, can comprise, for example, from 1.0 to 1000 mg, typically from 10 to 600 mg. In the case of pharmaceutically tolerated salts, the abovementioned weight data relate to the weight of the benzothiazepine ion derived from the salt.

For prophylaxis or treatment of the abovementioned states, compounds according to formula (I) can be used themselves as the compound, but they are preferably present in the form of a pharmaceutical composition with a tolerated excipient. The excipient must of course be tolerated, in the sense that it is compatible with the other constituents of the composition and does not harm the health of the patient. The excipient can be a solid or a liquid or both, and is preferably formulated with the compound as an individual dose, for example as a tablet, which can comprise from 0.05% to 95% by weight of the active compound. Further pharmaceutically active substances can likewise be present, including further compounds according to formula (I). The pharmaceutical compositions according to the invention can be prepared by one of the known pharmaceutical methods, which substantially comprise mixing the constituents with pharmacologically tolerated excipients and/or auxiliaries.

Pharmaceutical compositions according to the present invention are those which are suitable for oral, rectal, topical, peroral (for example sublingual) and parenteral (for example subcutaneous, intramuscular, intradermal or intravenous) administration, although the most suitable mode of administration in each individual case depends on the nature and severity of the condition to be treated and on the nature of the particular compound(s) according to formula (I) used. Coated formulations and coated sustained-release formulations also belong in the context of the invention. Formulations which are resistant to acid and gastric juice are preferred. Suitable coatings which are resistant to gastric juice include cellulose acetate phthalate, polyvinyl acetate phthalate, hydroxypropyl methylcellulose phthalate and anionic polymers of methacrylic acid and methyl methacrylate.

Suitable pharmaceutical compounds for oral administration can exist in separate units, such as, for example, capsules, cachets, sucking tablets or tablets, each of which comprises a certain amount of a compound according to formula (I); as powders or granules; as a solution or suspension in an aqueous or nonaqueous liquid; or as an oil-in-water or water-in-oil emulsion, As already mentioned, these formulations can be prepared by any suitable pharmaceutical method which comprises a step in which the active compound and the excipient (which can comprise one or more additional constituents) are brought into contact. In general, the compositions are prepared by uniform and homogeneous mixing of the active compound with a liquid and/or finely divided solid excipient, after which the product is shaped, if necessary. Thus, for example, a tablet can be prepared by pressing or shaping a powder or granules of the compound, optionally with one or more additional constituents. Pressed tablets can be prepared by tabletting the compound in a free-flowing form, such as, for example, a powder or granules, optionally mixed with a binder, lubricant, inert diluent and/or one (or more) surface-active/dispersing agent(s), in a suitable machine. Shaped tablets can be prepared by shaping the pulverulent compound, which has been moistened with an inert liquid diluent, in a suitable machine.

Pharmaceutical compositions which are suitable for a peroral (sublingual) administration include sucking tablets which comprise a compound of formula (I) with a flavoring substance, usually sucrose, and gum arabic or tragacanth, and pastilles which comprise the compound in an inert base, such as gelatin, and glycerol or sucrose and gum arabic.

Suitable pharmaceutical compositions for parenteral administration preferably include sterile aqueous formulations of a compound according to formula (I), which are preferably isotonic with the blood of the intended recipient. These formulations are preferably administered intravenously, although the administration can also take place subcutaneously, intramuscularly or intradermally as an injection. These formulations can preferably be prepared by mixing the compound with water and rendering the resulting solution sterile and isotonic with blood. Injectable compositions according to the invention in general comprise from 0.1 to 5% by weight of the active compound.

Suitable pharmaceutical compositions for rectal administration are preferably in the form of individual-dose suppositories. These can be prepared by mixing a compound according to formula (I) with one or more conventional solid excipients, for example cocoa butter, and shaping the mixture formed.

Suitable pharmaceutical compositions for topical application to the skin are preferably in the form of an ointment, cream, lotion, paste, spray, aerosol or oil. Petroleum jelly, lanolin, polyethylene glycols, alcohols and combinations of two or more of these substances can be used as excipients. The active compound is in general present in a concentration of 0.1 to 15% by weight of the composition, for example 0.5 to 2%.

A transdermal administration is also possible. Suitable pharmaceutical compositions for transdermal applications can be in the form of individual patches which are suitable for long-term close contact with the epidermis of the patient. Such patches suitably comprise the active compound in an optionally buffered aqueous solution, dissolved and/or dispersed in an adhesion promoter or dispersed in a polymer. A suitable active compound concentration is about 1% to 35%, preferably about 3% to 15%. As a particular possibility, the active compound can be released by electrotransportation or iontophoresis, as described, for example, in *Pharmaceutical Research*, 2(6): 318 (1986).

The invention relates to compounds of formula (I) in the form of their racemates, racemic mixtures and pure enantiomers and to their diastereomers and mixtures thereof.

The alkyl, alkenyl and alkynyl radicals in the substituents $R^1$, $R^2$, $R^3$, and $R^4$ can be either straight-chain or branched.

The compounds of formula (I) and pharmaceutically tolerated salts and physiologically functional derivatives thereof are distinguished by favorable actions on lipid metabolism. The compounds can be employed by themselves or in combination with further lipid-lowering active compounds. The compounds are suitable for prophylaxis and, in particular, for treatment of disturbances in lipid metabolism, in particular hyperlipidemia. The compounds of the formula (I) are also suitable for influencing the serum cholesterol level and for prevention and treatment of arteriosclerotic symptoms.

The following findings demonstrate the pharmacological activity and utility of the compounds according to the invention.

Biological testing of the compounds according to the invention was carried out by determining the inhibition of [$^3$H]-taurocholate uptake in brush border membrane vesicles of the ileum of rabbits. The inhibition test was carried out as described below.

Test 1. Preparation of Brush Border Membrane Vesicles from the Ileum of Rabbits

Brush border membrane vesicles from the intestinal cells of the small intestine were prepared by the so-called $Mg^{2+}$ precipitation method as follows. Male New Zealand rabbits (2 to 2.5 kg body weight) were sacrificed by intravenous injection of 0.5 ml of T61®, an aqueous solution of 2.5 mg of tetracaine HCl, 100 mg of embutramide and 25 mg of mebezonium iodide. The small intestine was removed and flushed with ice-cold physiological saline solution. The terminal 7/10 of the small intestine (measured in the oral-rectal direction, i.e. the terminal ileum, which contains the active $Na^+$-dependent bile acid transportation system) was used for preparation of the brush border membrane vesicles. The intestines were frozen in plastic bags under nitrogen at −80° C.

For preparation of the membrane vesicles, the frozen intestines were thawed at 30° C. in a water-bath. The mucosa were peeled off and suspended in 60 ml of ice-cold 12 mM TRIS-HCl buffer (pH 7.1)/300 mM mannitol, 5 mM EGTA/ 10 mg/l of phenylmethyl-sulfonyl fluoride/1 mg/l of trypsin inhibitor from soybeans (32 U/mg)/0.5 mg/l of trypsin inhibitor from the bovine lung (193 U/mg)/5 mg/l of bacitracin. After dilution to 300 ml with ice-cold distilled water, the mixture was homogenized with an Ultraturrax (18-rod, IKA Werk Staufen, Germany) for 3 minutes at 75% of the maximum power, while cooling with ice. After addition of 3 ml of 1 M $MgCl_2$ solution (final concentration 10 mM), the mixture was left to stand for exactly 1 minute at 0° C. The cell membranes aggregated by addition of $Mg^{2+}$ and precipitated, with the exception of the brush border membranes. After centrifugation for 15 minutes at 3000×g (5000 rpm, SS-34 rotor), the precipitate was discarded and the supernatant, which contained the brush border membranes, was centrifuged at 48000×g (20000 rpm, SS-34 rotor) for 30 minutes. The supernatant was discarded and the precipitate was rehomogenized in 60 ml of 12 mM TRIS/HCl buffer (pH 7.1)/60 mM mannitol, 5 mM EGTA with a Potter Elvejhem homogenizer (Braun, Melsungen, 900 rpm, 10-stroke). After addition of 0.1 ml of 1 M $MgCl_2$ solution and an incubation time of 15 minutes at 0° C., the mixture was centrifuged again at 3000×g for 15 minutes. The supernatant was then centrifuged again at 48000×g (20000 rpm, SS-34 rotor) for 30 minutes. The precipitate was taken up in 30 ml of 10 mM TRIS/HEPES buffer (pH 7.4)/300 mM mannitol and resuspended by 20 strokes in a Potter Elvejhem homogenizer at a 1000 rpm. After centrifugation at 48000×g (20000 rpm, SS-34 rotor) for 30 minutes, the precipitate was taken up in 0.5 to 2 ml of TRIS/HEPES buffer (pH 7.4)/280 mM mannitol (final concentration 20 mg/ml) and resuspended with the aid of a tuberculin syringe with a 27-gauge needle. The vesicles were either used for the transportation investigations directly after the preparation, or stored in 4 mg portions in liquid nitrogen at −196° C.

Test 2. Inhibition of the $Na^+$-dependent [$^3$H]Taurocholate Uptake in Brush Border Member Vesicles of the Ileum The uptake of substrates into the brush border membrane vesicles described above was determined by means of the so-called membrane filtration technique. 10 μl of the vesicle suspension (100 μg of protein) were pipetted as drops onto the wall of a polystyrene incubation tube (11×70 mm) which contained the incubation medium with the corresponding ligands (90 μl). The incubation medium comprised 0.75 μl=0.75 μCi [$^3$H(G)]-taurocholate (specific activity: 2.1 Ci/mmol)/0.5 μl of 10 mM taurocholate/8.75 μl of sodium transportation buffer (10 mM TRIS/HEPES, (pH 7.4)/100 mM mannitol/100 mM NaCl) (Na-T-B) or 8.75 μl of potassium transportation buffer (10 mM TRIS/HEPES (pH 7.4)/ 100 mM mannitol/100 mM KCl) (K-T-B) and 80 μl of the inhibitor solution in question, dissolved in Na-T buffer or K-T buffer, depending on the experiment. The incubation medium was filtered through a polyvinylidene fluoride membrane filter (SYHV LO 4NS, 0.45 μm, 4 mm Ø, Millipore, Eschborn, Germany). The transportation measurement was started by mixing the vesicles with the incubation medium. The concentration of taurocholate in the incubation batch was 50 μM. After the desired incubation time (usually 1 minute), the transportation was stopped by addition of 1 ml of ice-cold stopping solution (10 mM TRIS/HEPES, (pH 7.4)/150 mM KCl). The mixture formed was immediately sucked over a membrane filter of cellulose nitrate (ME 25, 0.45 μm, 25 mm diameter, Schleicher & Schuell, Dassell, Germany) under a vacuum of 25 to 35 mbar. The filter was rinsed with 5 ml of ice-cold stopping solution.

To measure the uptake of the radioactively labelled taurocholate, the membrane filter was dissolved with 4 ml of the scintillator Quickszint 361 (Zinsser Analytik GmbH, Frankfurt, Germany) and the radioactivity was measured by liquid scintillation measurement in a TriCarb 2500 measuring apparatus (Canberra Packard GmbH, Frankfurt, Germany). The values measured were obtained as dpm (decompositions per minute), after calibration of the apparatus with the aid of standard samples and after correction of any chemiluminescence present.

The control values were each determined in Na-T-B and K-T-B. The difference between the uptake in Na-T-B and K-T-B gave the Na⁺-dependent transportation content. $IC_{50}$ Na⁺ represents the concentration of inhibitor at which the Na⁺-dependent transporation content was inhibited by 50%, based on control values.

The pharmacological data comprise a test series in which the interaction of the compounds according to the invention with the intestinal bile acid transportation system in the terminal small intestine was investigated. The results are summarized in Table 1.

Test Results

Table 1 shows measured values (biological test) of the inhibition of [³H]-taurocholate uptake in brush border membrane vesicles of the ileum of rabbits. The quotients of the $IC_{50Na}$ values of the reference substance as taurochenodeoxycholate (TCDC) and of the particular test substance are stated.

The following examples serve to illustrate the invention in more detail, without limiting this to the products and embodiments described in the examples.

The compounds shown in Table 1 are diastereomers which are in the form of racemates. In the Isomer column, the relative polarity of the particular diastereomer is stated, the higher number correlating with a low $R_f$ value. It can be seen from the table that the compounds of formula (I) show a good lipid-lowering action.

TABLE 1

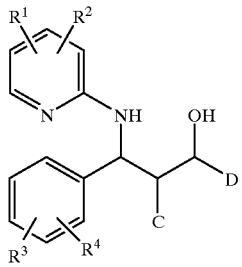

| Ex. | R¹ | R² | R³ | R⁴ | C | D | Isomer | Empirical formula (molecular weight) | MS | Melting point (° C.) | Biological Test |
|---|---|---|---|---|---|---|---|---|---|---|---|
| 1 | H | H | H | H | Quinolin-2-yl | Phenyl | II | C₂₉H₂₅N₃O (431.5) | 432.1 M+H⁺ | 187 | |
| 2 | H | H | H | H | Quinolin-2-yl | Phenyl | I | C₂₉H₂₅N₃O (431.5) | 432.1 M+H⁺ | <100 | 0.83 |
| 3 | H | H | H | H | Phenyl | Thiazol-2-yl | I | C₂₃H₂₁N₃OS (387.5) | 388.2 M+H⁺ | 204 | |
| 4 | H | H | H | H | Phenyl | Thiazol-2-yl | II | C₂₃H₂₁N₃OS (387.5) | 388.2 M+H⁺ | <100 | 0.1 |
| 5 | H | H | H | H | Phenyl | Thiazol-2-yl | III | C₂₃H₂₁N₃OS (387.5) | 388.2 M+H⁺ | 204 | |
| 6 | H | H | H | H | Quinoxalin-2-yl | Phenyl | I | C₂₈H₂₄N₄O (432.5) | 433.2 M+H⁺ | — | 0.57 |
| 7 | H | H | H | H | Quinoxalin-2-yl | Phenyl | II | C₂₈H₂₄N₄O (432.5) | 433.2 M+H⁺ | 150 | 0.22 |
| 8 | H | H | H | H | Quinolin-3-yl | Phenyl | I | C₂₉H₂₅N₃O (431.5) | 432.2 M+H⁺ | 210 | |
| 9 | H | H | H | H | Quinolin-3-yl | Phenyl | II | C₂₉H₂₅N₃O (431.5) | 432.2 M+H⁺ | Oil | 0.35 |
| 10 | H | H | H | H | Phenyl | Benzohiazol-2-yl | I | C₂₇H₂₃N₃OS (437.6) | 438.2 M+H⁺ | 183 | |
| 11 | H | H | H | H | Pyrid-2-yl | 1,4-pyrimidin-2-yl | I | C₂₃H₂₁N₅O (383.5) | 384.2 M+H⁺ | Oil | 0.24 |
| 12 | H | H | H | H | Pyrid-2-yl | 1,4-Pyrimidin-2-yl | II | C₂₃H₂₁N₅O (383.5) | 384.2 M+H⁺ | <100 | 0.24 |
| 13 | H | H | H | H | Pyrid-2-yl | 5-Methyl-1,4-pyrimidin-2-yl | I | C₂₄H₂₃N₅O (397.5) | 398.2 M+H⁺ | 140 | |
| 14 | H | H | H | H | Pyrid-2-yl | 2,4-Dimethyl-thiazol-5-yl | I | C₂₄H₂₄N₄OS (416.6) | 417 2 M+H⁺ | 154 | 0.66 |
| 15 | H | H | H | H | Pyrid-2-yl | 2,4-Dimethyl-thiazol-5-yl | 11 | C₂₄H₂₄N₄OS (416.6) | 417.2 M+H⁺ | 184 | |
| 16 | H | H | H | H | Pyrid-2-yl | 2,4-Dimethyl-thiazal-5-yl | III | C₂₄H₂₄N₄OS (416.6) | 417.2 M+H⁺ | 191 | |
| 17 | H | H | H | H | Pyrid-2-yl | 4,5,6,7-tetrahydrobenz-isoxazol-3-yl | I | C₂₆H₂₆N₄O₂ (426.5) | 427.3 M+H⁺ | 207 | |
| 18 | H | H | H | H | Pyrid-2-yl | Quinoln-3-yl | I | C₂₈H₂₄N₄O (432.5) | 433.3 M+H⁺ | 164 | 0.37 |
| 19 | H | H | H | H | Pyrid-2-yl | Quinolin-3-yl | II | C₂₈H₂₄N₄O (432.5) | 433.3 M+H | 199 | 0.42 |
| 20 | H | H | H | H | Pyrid-2-yl | Quinolin-3-yl | III | C₂₈H₂₄N₄O (432.5) | 433.3 M+H⁺ | 146 | 0.23 |
| 21 | H | H | H | H | Pyrid-2-yl | Thien-2-yl | I | C₂₃H₂₁N₃OS | 388.3 | 156 | 1.16 |

TABLE 1-continued

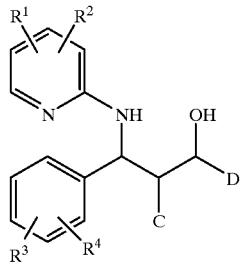

| Ex. | $R^1$ | $R^2$ | $R^3$ | $R^4$ | C | D | Isomer | Empirical formula (molecular weight) | MS | Melting point (° C.) | Biological Test |
|---|---|---|---|---|---|---|---|---|---|---|---|
| 22 | H | H | H | H | Pyrid-2-yl | Thien-2-yl | II | $C_{23}H_{21}N_3OS$ (387.5) | 388.2 M+H$^+$ | 166 | 0.19 |
| 23 | H | H | H | H | Pyrid-2-yl | Thien-2-yl | III | $C_{23}H_{21}N_3OS$ (387.5) | 388.2 M+H$^+$ | 171 | 0.23 |
| 24 | H | H | H | H | Pyrid-2-yl | Thien-2-yl | IV | $C_{23}H_{21}N_3OS$ (387.5) | 388.2 M+H$^+$ | 123 | 0.22 |
| 25 | H | H | H | H | Pyrid-2-yl | 2,5-Dimethyloxazol-4-yl | I | $C_{24}H_{24}N_4O_2$ (400.5) | 401.3 M+H$^+$ | 161 | 0.46 |
| 26 | H | H | H | H | Pyrid-2-yl | 5-Chlorothien-2-yl | I | $C_{23}H_{20}ClN_3OS$ (422.0) | 422.2 M+H$^+$ | 136 | 0.26 |
| 27 | H | H | H | H | Pyrid-2-yl | 5-Methylthien-2-yl | I | $C_{24}H_{23}N_3OS$ (401.5) | 402.2 M+H$^+$ | 115 | 1.02 |
| 28 | H | H | H | H | Pyrid-2-yl | 5-Methylthien-2-yl | II | $C_{24}H_{23}N_3OS$ (401.5) | 402.2 M+H$^+$ | 134 | |
| 29 | H | H | H | H | Pyrid-2-yl | 5-Methylthien-2-yl | III | $C_{24}H_{23}N_3OS$ (401.5) | 402.2 M+H$^+$ | 183 | |
| 30 | H | H | H | H | Pyrid-2-yl | 5-Methylthien-2-yl | IV | $C_{24}H_{23}N_3OS$ (401.5) | 402.2 M+H$^+$ | 169 | |
| 31 | H | H | H | H | Pyrid-2-yl | 3,5-Dimethylisoxazol-4-yl | I | $C_{24}H_{24}N_4O_4$ (400.5) | 401.3 M+H$^+$ | 153 | 0.37 |
| 32 | H | H | H | H | Pyrid-2-yl | 2-Ethyl-4-methyloxazol-5-yl | I | $C_{25}H_{26}N_4O_2$ (414.5) | 41 5.3 M+H$^+$ | 98 | |
| 33 | H | H | H | H | Pyrid-2-yl | 4,5-Dimethylthiazol-2-yl | I | $C_{24}H_{24}N_4OS$ (416.6) | 417.3 M+H $^+$ | 135 | 0.24 |
| 34 | H | H | 2-NO$_2$ | H | Pyrid-2-yl | 2,4-Dimethylthiazol-5-yl | I | $C_{24}H_{23}N_5O_3S$ (461.6) | 462.1 M+H$^+$ | 182 | |
| 35 | H | H | H | H | Pyrid-2-yl | Oxazol-4-yl | I | $C_{22}H_{26}N_4O_2$ (372.4) | 373.1 M+H$^+$ | 159 | |
| 36 | H | H | H | H | Pyrid-2-yl | 3-Methyl-5-phenyl-isoxazol-4-yl | I | $C_{29}H_{26}N_4O_2$ (462.6) | 463.3 M+H$^+$ | 178 | |
| 37 | H | H | H | H | Pyrid-2-yl | 3-Methoxythien-2-yl | I | $C_{24}H_{23}N_3O_2S$ (417.5) | 418.3 M+H$^+$ | 120 | 9.53 |
| 38 | H | H | 2-NO$_2$ | H | Pyrid-2-yl | 2,4-Dimethylthiazol-5-yl | I | $C_{24}H_{23}N_5O_3S$ (461.6) | 462.2 M+H$^+$ | 174 | |
| 39 | H | H | 2-NH$_2$ | H | Pyrid-2-yl | 2,4-Dimethylthiazol-5-yl | I | $C_{24}H_{25}N_5OS$ (431.6) | 432.2 M+H$^+$ | 127 | 0.65 |
| 40 | H | H | H | H | Pyrid-2-yl | 5-Pentylisoxazol-3-yl | I | $C_{27}H_{30}N_4O_2$ (442.6) | 443.3 M+H$^+$ | 120 | |
| 41 | H | H | H | H | Pyrid-2-yl | 5-Phenylisoxazol-3-yl | I | $C_{28}H_{24}N_4O_2$ (448.5) | 449.3 M+H$^+$ | 195 | 0.60 |
| 42 | H | H | H | H | Pyrid-2-yl | 1-Methyl-1,3-imidazol-2-yl | I | $C_{23}H_{23}N_5O$ (385.5) | 386.2 M+H$^+$ | 218 | 0.87 |
| 43 | H | H | 2-NO$_2$ | H | Pyrid-2-yl | 3,5-Dimethylisoxazol-4-yl | I | $C_{24}H_{23}N_5O_4$ (445.5) | 446.3 M+H$^+$ | 95 | 0.23 |
| 44 | H | H | 2-NH$_2$ | H | Pyrid-2-yl | 3,5-Dimethylisoxazol-4-yl | I | $C_{24}H_{25}N_5O_2$ (415.5) | 416.4 M+H$^+$ | 130 | 0.74 |
| 45 | H | H | H | H | Pyrid-2-yl | 5-Methylisoxazol-3-yl | I | $C_{23}H_{22}N_4O_2$ (386.5) | 387.2 M+H$^+$ | — | |
| 46 | H | H | H | H | Pyrid-2-yl | Indol-2-yl | I | $C_{27}H_{24}N_4O$ (420.5) | 421.2 M+H$^+$ | 209 | 0.22 |
| 47 | H | H | H | H | Pyrid-2-yl | 1-Methyl-1,2,4-triazol-5-yl | I | $C_{22}H_{22}N_6O$ (386.5) | 387.2 M+H$^+$ | 210 | 0.35 |
| 48 | H | H | 2-NH$_2$ | H | Pyrid-2-yl | 2,5-Dimethyloxazol-4-yl | I | $C_{24}H_{25}N_5O_2$ (415.5) | 416.3 M+H$^+$ | 112 | 0.80 |
| 49 | H | H | 2-NH$_2$ | H | Pyrid-2-yl | 5-Methylisoxazol-3-yl | I | $C_{23}H_{23}N_5O_2$ (401.5) | 402.3 M+H$^+$ | foam | 0.77 |
| 50 | H | H | H | H | Pyrid-2-yl | 4-Methyl-2-pyrid-4-yl thiazol-5-yl | I | $C_{28}H_{25}N_5OS$ (479.6) | 480.2 M+H$^+$ | 146 | 0.79 |
| 51 | H | H | H | H | Pyrid-2-yl | 4-Methyl-2-prid-4-yl | II | $C_{28}H_{25}N_5OS$ | 480.2 | 186 | 0.52 |

TABLE 1-continued

![structure with R1, R2 on pyridine-NH, R3, R4 on phenyl, C and D substituents with OH]

| Ex. | R¹ | R² | R³ | R⁴ | C | D | Isomer | Empirical formula (molecular weight) | MS | Melting point (° C.) | Biological Test |
|---|---|---|---|---|---|---|---|---|---|---|---|
| 52 | H | H | H | H | Pyrid-2-yl | 4-Methyl-2-prid-4-yl thiazol-5-yl | III | $C_{28}H_{25}N_5OS$ (479.6) | 480.2 M+H⁺ | foam | 0.40 |
| 53 | H | H | H | H | Pyrid-2-yl | Isoxazol-3-yl | I | $C_{22}H_{20}N_4O_2$ (372.4) | 373.2 M+H⁺ | 87 | |
| 54 | H | H | H | H | Pyrid-2-yl | 5-Methyl-3-(3-tri-fluoromethylphenyl)-isoxazol-4-yl | I | $C_{30}H_{25}F_3N_4O_2$ (530.6) | 531.2 M+H⁺ | oil | |
| 55 | H | H | 2-NH₂ | H | Pyrid-2-yl | Isoxazol-3-yl | I | $C_{22}H_{21}N_5O_2$ (387.4) | 388.2 M+H⁺ | 156 | 0.31 |
| 56 | H | H | 2-NH₂ | H | Pyrid-2-yl | 3-(3-Chlorophenyl)-5-methylisoxazol-4-yl | I | $C_{29}H_{26}ClN_5O_2$ (512.0) | 512.2 M+H⁺ | oil | |
| 57 | H | H | 2-NH₂ | H | Pyrid-2-yl | 4-Methyl-2-pyrid-4-yl-thiazol-5-yl | I | $C_{28}H_{26}N_6OS$ (494.6) | 497.2 M+H⁺ | 135 | |
| 58 | H | H | H | 2-NO₂ | Benzothiazol-2-yl | Phenyl | I | $C_{27}H_{22}N_4O_3S$ (482.14) | 483.2 M+H⁺ | 178 | |
| 59 | H | H | H | 2-NO₂ | Benzothiazol-2-yl | Phenyl | II | $C_{27}H_{22}N_4O_3S$ (482.14) | 483.2 M+H⁺ | 153 | |
| 60 | H | H | H | H | 5-Methyl-thien-2-yl | Phenyl | I | $C_{25}H_{24}N_2OS$ (400.16) | 401.2 M+H⁺ | 165 | |
| 61 | H | H | H | H | 5-Methyl-thien-2-yl | Phenyl | II | $C_{25}H_{24}N_2OS$ (400.16) | 401.2 M+H⁺ | 155 | |
| 62 | H | H | H | H | Benzothiazol-2-yl | Phenyl | I | $C_{27}H_{23}N_3OS$ (437.16) | 438.2 M+H⁺ | 80 | |
| 63 | H | H | H | H | 5-Methyl-thiazol-2-yl | Phenyl | I | $C_{24}H_{23}N_3OS$ (401.16) | 402.2 M+H⁺ | 142 | |
| 64 | H | H | H | H | 5-Methyl-thiazol-2-yl | Phenyl | II | $C_{24}H_{23}N_3OS$ (401.16) | 402.2 M+H⁺ | — | |
| 65 | H | H | H | H | 2-Nitro-3 thienyl | Phenyl | I | $C_{24}H_{21}N_3O_3S$ (431.13) | 432.1 M+H⁺ | 215 | |

The preparation of some examples is described in detail below, and the other compounds of formula (I) (see Table 1) were obtained analogously from corresponding starting compounds:

EXAMPLE A

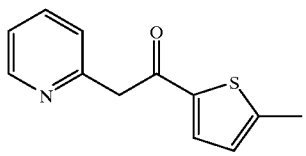

38 ml of 15% strength n-butyllithium in n-hexane were added dropwise to 5.6 g (0.06 mol) of picoline in 50 ml of absolute tetrahydrofuran at −60° C. The mixture was warmed to room temperature and cooled again to −60° C. 8.5 g of 5-methylthiophene-2-carboxylic acid (0.05 mol) in 15 ml of tetrahydrofuran were slowly added dropwise and the mixture was then warmed to room temperature and stirred for an additional hour. After addition of 300 ml of water, and neutralization by means of 20% strength aqueous citric acid solution, the mixture was extracted three times with 100 ml of methylene chloride, and the organic phases were dried with Na₂SO₄ and evaporated under reduced pressure. After chromatography over silica gel with n-heptane/ethyl acetate as the mobile phase, 2.6 g (24% of theory) of the reaction product were obtained in the form of a pale yellow oil.

$C_{12}H_{11}NOS$ (217.3) MS 218.2 M+H⁺

EXAMPLE B

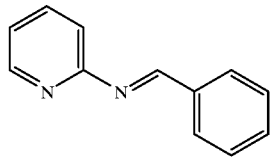

51 ml (0.5 mol) of benzaldehyde, 47 g (0.5 mol) of 2-aminopyridine and 1 g of p-toluenesulfonic acid were dissolved in 400 ml of toluene and the solution was heated under reflux for 3 hours using a water separator. The solution was cooled and the organic phase was washed twice with saturated aqueous NaHCO$_3$ solution and twice with 100 ml of water each time. It was then dried with Na$_2$SO$_4$ and concentrated under reduced pressure. The crude product, obtained as an oil, was distilled under an oil pump vacuum.

Yield: 73.8 g (81% of theory) of product
Boiling point$_{0.2}$: 125° C.
C$_{12}$H$_{12}$N$_2$ (182.2) MS 183.3 M+H$^+$

EXAMPLE C

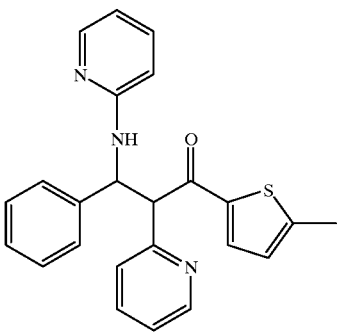

(Mixture of Two Diastereomers)

2.6 g (12 mmol) of ketone from Example 1 a and 2.2 g (12 mmol) of imine from Example 1 b were dissolved in 50 ml of ethanol. After a few minutes, a colorless solid started to precipitate out. The mixture was stirred at room temperature for 48 hours to bring the reaction to completion. After cooling, the precipitate was filtered off with suction and recrystallized from ethanol.

Yield: 3.45 g (72% of theory) of product
Melting point: 160° C.

EXAMPLE D

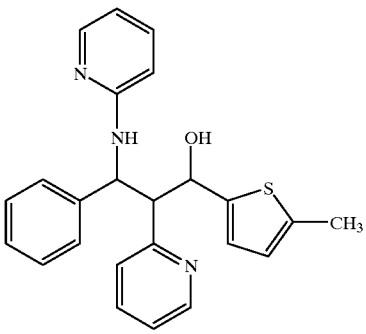

(Preparation of the Four Possible Diastereomers, See Examples 27 to 30, Table 1)

3.4 g (8.5 mmol) of the keto compound from Example 1 c were dissolved in a mixture of 350 ml of methylene chloride, 25 ml of methanol and 8 ml of water. 2.4 g of sodium borohydride were added and the mixture was stirred at room temperature for 5 hours. The solution was then extracted twice with 150 ml of water and the organic phase was dried with Na$_2$SO$_4$ and evaporated. The residue was chromatographed over silica gel (n-heptane/ethyl acetate 1:1). Four compounds, each racemic, were obtained as colorless crystalline products:

1st fraction:
  1.1 g (32%) of highly nonpolar racemate (Example 27);
  R$_f$(ethyl acetate/n-heptane=1/1): 0.37
  Melting point: 115° C.
  C$_{24}$H$_{23}$N$_3$OS (401.5) MS (FAB) 402.2 M+H$^+$ 2nd fraction:
  0.32 g (9%) of nonpolar racemate (Example 28)
  R$_f$(ethyl acetate/n-heptane=1/1): 0.30
  Melting point: 134° C.
  C$_{24}$H$_{23}$N$_3$OS (401.5) MS (FAB) 402.2 M+H$^+$ 3rd fraction:
  0.54 g (16%) of moderately polar racemate (Example 29)
  R$_f$(ethyl acetate/n-heptane=1/1): 0.22
  Melting point: 183° C.
  C$_{24}$H$_{23}$N$_3$OS (401.5) MS (FAB) 402.2 M+H$^+$ 4th fraction:
  0.38 (11%) of polar racemate (Example 30)
  R$_f$(ethyl acetate/n-heptane=1/1): 0.16
  Melting point: 169° C.
  C$_{24}$H$_{23}$N$_3$OS (401.5) MS (FAB) 402.2 M+H$^+$ The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

We claim:

1. A compound of formula (I), or a salt thereof,

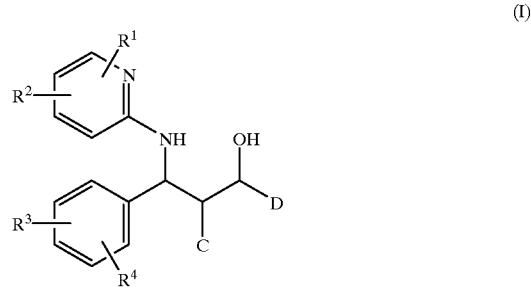

wherein:
  C is phenyl, pyridyl, thienyl, furyl, pyrimidyl, indolyl, thiazolyl, imidazolyl, coumarinyl, phthalimidyl, quinolyl, piperazinyl, tetrazolyl, triazolyl, oxazolyl, isoxazolyl, isothiazolyl, or thieno-, pyridino-, or benzo-fused derivatives thereof, wherein the aromatic or heteroaromatic radical is unsubstituted, or is mono- or disubstituted by fluorine, chlorine, bromine, iodine, —OH, —CF$_3$, —NO$_2$, —CN, —(C$_1$–C$_8$)-alkoxy, —(C$_1$–C$_8$)-alkyl, —NH$_2$, —NH—R$^9$, —N(R$^9$)R$^{10}$, —CHO, —COOH, —COOR$^{11}$, —(C=O)—R$^{12}$, —(C$_1$–C$_6$)-alkyl-OH, —(C$_1$–C$_6$)-alkyl(—OH)-phenyl, —(C$_1$–C$_6$)-alkyl-CF$_3$, —(C$_1$–C$_6$)-alkyl-NO$_2$, —(C$_1$–C$_6$)-alkyl-CN, —(C$_1$–C$_6$)-alkyl-NH$_2$, —(C$_1$–C$_6$)-alkyl-NH—R$^9$, —(C$_1$–C$_6$)-alkyl-N(R$^9$)R$^{10}$, —(C$_1$–C$_6$)-alkyl-CHO, —(C$_1$–C$_6$)-alkyl-COOH, —(C$_1$–C$_6$)-alkyl-COOR$^{11}$, —(C$_1$–C$_6$)-alkyl-(C=O)—R$^{12}$, —O—(C$_1$–C$_6$)-alkyl-OH, —O—(C$_1$–C$_6$)-alkyl-CF$_3$, —O—(C$_1$–C$_6$)-alkyl-NO$_2$, —O—(C$_1$–C$_6$)-alkyl- CN, —O—($C_1$–$C_6$)-alkyl-$NH_2$, —O—($C_1$–$C_6$)-alkyl-NH—$R^9$, —O—($C_1$–$C_6$)-alkyl-N($R^9$)$R^{10}$, —O—($C_1$–$C_6$)-alkyl-CHO, —O—($C_1$–$C_6$)-alkyl-COOH, —O—($C_1$–$C_6$)-alkyl-$COOR^{11}$, —O—($C_1$–$C_6$)-alkyl-(C=O)—$R^{12}$, —N—$SO_3H$, —$SO_2$—$CH_3$, or —O—($C_1$–$C_6$)-alkyl-O—($C_1$–$C_6$)-alkylphenyl, wherein one or more hydrogens(s) in the alkyl radicals is optionally replaced by fluorine;

D is thienyl, furyl, thiazolyl, imidazolyl, tetrazolyl, triazolyl, oxazolyl, isoxazolyl, or isothiazolyl, wherein the heteroaromatic radical is unsubstituted, or in mono- or disubstituted by fluorine, chlorine, bromine, iodine, —OH, —$CF_3$, —$NO_2$, —CN, —($C_1$–$C_8$)-alkoxy, —($C_1$–$C_8$)-alkyl, —$NH_2$, —NH—$R^9$, N($R^9$)$R^{10}$, —CHO, —COOH, —$COOR^{11}$, —(C=O)—$R^{12}$, —($C_1$–$C_6$)-alkyl-OH, ($C_1$–$C_6$)-alkyl(—OH)-phenyl, ($C_1$–$C_6$)-alkyl-$CF_3$, —($C_1$–$C_6$)-alkyl-$NO_2$,—($C_1$–$C_6$)-alkyl-CN, —($C_1$–$C_6$)-alkyl-$NH_2$, —($C_1$–$C_6$)-alkyl-NH—$R^9$, —($C_1$–$C_6$)-alkyl-N($R^9$)$R^{10}$, ($C_1$–$C_6$)-alkyl-CHO, —($C_1$–$C_6$)-alkyl-COOH, —($C_1$–$C_6$)-alkyl-$COOR^{11}$, —($C_1$–$C_6$)-alkyl-(C=O)—$R^{12}$, —O—($C_1$–$C_6$)-alkyl-OH, —O—($C_1$–$C_6$)-alkyl-$CF_3$, —O—($C_1$–$C_6$)-alkyl-$NO_2$, —O—($C_1$–$C_6$)-alkyl-CN, —O—($C_1$–$C_6$)-alkyl-$NH_2$, —O—($C_1$–$C_6$)-alkyl-NH—$R^9$, —O—($C_1$–$C_6$)-alkyl-N($R^9$)$R^{10}$, —O—($C_1$–$C_6$)-alkyl-CHO, —O—($C_1$–$C_6$)-alkyl-COOH, —O—($C_1$–$C_6$)-alkyl-$COOR^{11}$, —O—($C_1$–$C_6$)-alkyl-(C=O)—$R^{12}$, —N—$SO_3H$, —$SO_2$—$CH_3$, —($C_0$–$C_6$)-alkyl-pyridyl, —O—($C_1$–$C_6$)-alkyl-O—($C_1$–$C_6$)-alkylphenyl, or —($C_0$–$C_6$)-alkylphenyl, wherein the phenyl radical is unsubstituted, or is mono- or disubstituted by F, Cl, —$CF_3$, —$OCF_3$, —($C_1$–$C_6$)-alkyl, or —O—($C_1$–$C_6$)-alkyl, and wherein one or more hydrogen(s) in the alkyl radicals is optionally replaced by fluorine;

$R^1$, $R^2$, $R^3$, $R^4$ each independently of one another is hydrogen, fluorine, chlorine, bromine, iodine, —OH, —$CF_3$, —$NO_2$, —CN, —($C_1$–$C_8$)-alkoxy, —($C_1$–$C_8$)-alkyl, —$NH_2$, —NH—$R^9$, N($R^9$)$R^{10}$, —CHO, —COOH, —$COOR^{11}$, (C=O)—$R^{12}$, —($C_1$–$C_6$)-alkyl-OH, —($C_1$–$C_6$)-alkyl(—OH)-phenyl, —($C_1$–$C_6$)-alkyl-$CF_3$, —($C_1$–$C_6$)-alkyl-$NO_2$, —($C_1$–$C_6$)-alkyl-CN, —($C_1$–$C_6$)-alkyl-$NH_2$, —($C_1$–$C_6$)-alkyl-NH—$R^9$,—($C_1$–$C_6$)-alkyl-N($R^9$)$R^{10}$, —($C_1$–$C_6$)-alkyl-CHO, —($C_1$–$C_6$)-alkyl-COOH, —($C_1$–$C_6$)-alkyl-$COOR^{11}$, —($C_1$–$C_6$)-alkyl-(C=O)—$R^{12}$, —O—($C_1$–$C_6$)-alkyl-OH, —O—($C_1$–$C_6$)-alkyl-$CF_3$, —O—($C_1$–$C_6$)-alkyl-$NO_2$, —O—($C_1$–$C_6$)-alkyl-CN, —O—($C_1$–$C_6$)-alkyl-$NH_2$, —O—($C_1$–$C_6$)-alkyl-NH—$R^9$, —O—($C_1$–$C_6$)-alkyl-N($R^9$)$R^{10}$, —O—($C_1$–$C_6$)-alkyl-CHO, —O—($C_1$–$C_6$)-alkyl-COOH, —O—($C_1$–$C_6$)-alkyl-$COOR^{11}$, —O—($C_1$–$C_6$)-alkyl-(C=O)—$R^{12}$, —N—$SO_3H$, —$SO_2$—$CH_3$, or —O—($C_1$–$C_6$)-alkyl-O—($C_1$–$C_6$)-alkylphenyl, wherein one or more hydrogen(s) in the alkyl radicals is optionally replaced by fluorine; and $R^9$ to $R^{12}$ each independently of one another is hydrogen or —($C_1$–$C_8$)-alkyl.

2. A compound of formula (I) or a salt thereof as claimed in claim 1, wherein:

C is phenyl, pyridyl, thienyl, furyl, pyrimidyl, indolyl, thiazolyl, imidazolyl, coumarinyl, phthalimidyl, quinolyl, piperazinyl, tetrazolyl, triazolyl, oxazolyl, isoxazolyl, isothiazolyl, or benzo-fused derivatives thereof, wherein the aromatic or heteroaromatic radical is unsubstituted, or is mono- or disubstituted by fluorine, chlorine, bromine, iodine, —OH, —$CF_3$, —$NO_2$, —CN, —($C_1$–$C_8$)-alkoxy, —($C_1$–$C_8$)-alkyl, —($C_3$–$C_6$)-cycloalkyl, —$NH_2$, —CHO, —COOH, or —$OCF_3$;

D is thienyl, furyl, thiazolyl, imidazolyl, tetrazolyl, triazolyl, oxazolyl, isoxazolyl, or isothiazolyl, wherein the heteroaromatic radical is unsubstituted, or is mono- or disubstituted by fluorine, chlorine, bromine, iodine, —OH, —$CF_3$, —$NO_2$, —CN, —($C_1$–$C_8$)-alkoxy, —($C_1$–$C_8$)-alkyl, —($C_3$–$C_6$)-cycloalkyl, —$NH_2$, —CHO, —COOH, or —$OCF_3$;

$R^1$, $R^2$, $R^3$, $R^4$ each independently of one another is hydrogen, fluorine, chlorine, bromine, iodine, —OH, —$CF_3$, —$OCF_3$, —$NO_2$, —CN, —($C_1$–$C_8$)-alkoxy, —($C_1$–$C_8$)-alkyl, —($C_3$–$C_6$)-cycloalkyl, —$NH_2$, —NH—$R_9$, —N($R^9$)$R^{10}$, —CHO, —COOH, —$COOR^{11}$, or —(C=)—$R^{12}$, wherein one or more hydrogen(s) in the alkyl radicals is optionally replaced by fluorine; and $R^9$ to $R^{12}$ each independently of one another is hydrogen or —($C_1$–$C_8$)-alkyl.

3. A compound of formula (I) or a salt thereof as claimed in claim 1, wherein:

C is phenyl, pyridyl, thienyl, pyrimidyl, indolyl, thiazolyl, quinolyl, oxazolyl, or isoxazolyl, wherein the aromatic or heteroaromatic radical is unsubstituted, or is mono— or disubstituted by fluorine, chlorine, bromine, or —($C_{1–C8}$)-alkyl;

D is thienyl, thiazolyl, imidazolyl, triazolyl, oxazolyl, or isoxazolyl, wherein the heteroaromatic radical is unsubstituted, or is mono- or disubstituted by fluorine, chlorine, bromine, or —($C_1$–$C_8$)-alkyl;

$R^1$, $R^2$, $R^3$, $R^4$ each independently of one another is hydrogen, fluorine, chlorine, bromine, iodine, —OH, —$CF_3$, —$OCF_3$, —$NO_2$, —CN, —($C_1$–$C_8$)-alkoxy, —($C_1$–$C_8$)-alkyl, —($C_3$–$C_6$)-cycloalkyl, —$NH_2$, —NH—$R^9$, —N($R^9$)$R^{10}$, —CHO, —COOH, —$COOR^{11}$, or —(C=O)—$R^{12}$, wherein one or more hydrogen(s) in the alkyl radicals is optionally replaced by fluorine; and $R^9$ to $R^{12}$ each independently of one another is hydrogen or —($C_1$–$C_8$)-alkyl.

4. A pharmaceutical composition, comprising at least one compound as claimed in claim 1 and a pharmacologically tolerated excipient.

5. The pharmaceutical composition of claim 4, further comprising at least one lipid-lowering active compound.

6. A method of preventing or treating disturbances in lipid metabolism, comprising administering to a patient in need thereof an effective amount of at least one compound as claimed in claim 1.

7. A method of treating hyperlipidemia, comprising administering to a patient in need thereof an effective amount of at least one compound as claimed in claim 1.

8. A method of preventing or treating arteriosclerotic symptoms, comprising administering to a patient in need thereof an effective amount of at least one compound as claimed in claim 1.

9. A method of preventing or treating disturbances in lipid metabolism, comprising administering to a patient in need thereof an effective amount of at least one compound as claimed in claim 1 in combination with at least one further lipid-lowering active compound.

10. A method of treating hyperlipidemia, comprising administering to a patient in need thereof an effective amount of at least one compound as claimed in claim 1 in combination with at least one further lipid-lowering active compound.

11. A method of preventing or treating arteriosclerotic symptoms, comprising administering to a patient in need thereof an effective amount of at least one compound as claimed in claim 1 in combination with at least one further lipid-lowering active compound.

12. A prodrug compound, which when administered to a mammal, forms a compound as claimed in claim 1.

* * * * *

UNITED STATES PATENT AND TRADEMARK OFFICE
CERTIFICATE OF CORRECTION

PATENT NO.   : 6,303,639 B1
DATED        : October 16, 2001
INVENTOR(S)  : Wendelin Frick et al.

It is certified that error appears in the above-identified patent and that said Letters Patent is hereby corrected as shown below:

Column 19,
Line 7, "hydrogens(s)" should read -- hydrogen(s) --.

Signed and Sealed this

Third Day of September, 2002

Attest:

JAMES E. ROGAN
Attesting Officer    Director of the United States Patent and Trademark Office